United States Patent [19]
Dirksing

[11] Patent Number: 5,125,886
[45] Date of Patent: * Jun. 30, 1992

[54] ONE PIECE POURING SPOUT SEALED TO INNERMOST AND OUTERMOST SURFACES OF MOISTURE IMPERVIOUS CARTON

[75] Inventor: William P. Dirksing, Cincinnati, Ohio

[73] Assignee: The Procter & Gamble Company, Cincinnati, Ohio

[ * ] Notice: The portion of the term of this patent subsequent to Mar. 20, 2007 has been disclaimed.

[21] Appl. No.: 451,495

[22] Filed: Dec. 15, 1989

[51] Int. Cl.⁵ ................................................ B31B 1/84
[52] U.S. Cl. ...................................... 493/87; 493/133; 264/23; 264/248; 264/249
[58] Field of Search .................... 493/85, 87, 102, 104, 493/133; 264/23, 25, 248, 249

[56] References Cited

U.S. PATENT DOCUMENTS

| | | | |
|---|---|---|---|
| 2,724,884 | 11/1955 | Jones | 264/249 |
| 4,411,720 | 10/1983 | Sager | 264/23 |
| 4,909,434 | 3/1990 | Jones et al. | 493/133 |

Primary Examiner—Bruce M. Kisliuk
Assistant Examiner—Jack Lavinder
Attorney, Agent, or Firm—E. Kelly Linman; Thomas H. O'Flaherty; Richard C. Witte

[57] ABSTRACT

A paperboard laminate carbon for containing a liquid product. The innermost and outermost surfaces of the carton are coated with a polymer which is both liquid impermeable and heat sealable. One of the walls of the carton includes an aperture which is fitted with an improved one-piece plastic spout. The spout, prior to installation, includes one preformed flange which contacts one surface of the carton about an aperture in the carton wall. A truncated skirt having a maximum cross-section small enough to pass through the aperture in the carton wall without damaging either the skirt or the carton wall extends from one surface of the preformed flange. A second flange is formed from the truncated skirt after the skirt has been inserted through the aperture in the carton wall.

Spout configurations which may be inserted from the exterior or the interior of the carton are disclosed. Because the flange which is formed from the truncated skirt exhibits a minimum cross-section greater than the maximum cross-section of the exterior portion of the spout, heat and pressure can be simultaneously applied to both the exterior and interior flanges in an area where the flanges coincide with one another without subjecting any other portions of the spout and/or resealable closure means to pressure. This permits easy and reliable simultaneous sealing of both flanges to the opposing surfaces of the carton wall in a single step.

8 Claims, 11 Drawing Sheets

ONE PIECE POURING SPOUT SEALED TO INNERMOST AND OUTERMOST SURFACES OF MOISTURE IMPERVIOUS CARTON

TECHNICAL FIELD

The present invention relates generally to packages, particularly cartons to be filled with liquid products such as milk, juice, beverages, laundry detergents, fabric softeners, etc.

The present invention has further relation to such liquid containing cartons comprised of paperboard or like materials which have been coated or otherwise protected to render their surfaces substantially impervious to moisture.

The present invention has further relation, in a particularly preferred embodiment, to a carton of the variety known as the gable top, having a double sloping top on a box-like body, with a pouring spout on one of the sloping sides through which the contained liquid is discharged.

The present invention has further relation to such cartons wherein the pouring spout is comprised of one piece and is sealed in liquid tight engagement to both the innermost and the outermost surfaces of the carton wall.

The present invention has further relation to such cartons wherein the pouring spout is provided with one preformed flange, the other flange being formed after a portion of the preformed spout has been inserted through a cut hole in the carton wall.

The present invention, in a particularly preferred embodiment, has further relation to such cartons wherein the liquid passageway initially present in said preformed spout comprises two distinct cross-sections, the first being defined by the discharge orifice in the spout and the second being defined by a truncated skirt depending from the lowermost surface of the preformed flange. Deformation of the truncated skirt depending from the lowermost surface of the preformed flange to form a second innermost flange facilitates simultaneous sealing of both the innermost and the outermost flanges of the spout to the opposing surfaces of the carton wall in a single step.

The present invention has still further relation to method and apparatus for securing said one-piece spout in sealed liquid-tight relation to both surfaces of the carton wall in a single step.

BACKGROUND OF THE INVENTION

The normal method of discharging a liquid from a gable top carton has been to open the sealed ridge of the gable by forcing its opposite sides away from each other. This practice has generally been found objectionable because of the considerable manual effort required as well as a potential hygienic problem, due to the need for direct manipulation of the gable top from which the liquid is to be poured. It also lacks tight reclosability, such as might be needed to shake a pulp-containing juice product without splashing.

Reusable carton holding and pouring devices to engage a gable top carton have been developed in an attempt to overcome some of these problems. For example, U.S. Pat. No. 4,723,689 issued to Vallos et al. on Feb. 9, 1988 discloses one such holder having a pouring spout including a blade which cuts a circular opening in the carton wall upon rotation of the spout. However, such holders are not always available each time a consumer desires to open and dispense a liquid product from a gable top carton.

Accordingly, considerable effort has been exerted to mount an opening/reclosing feature, such as a plastic mouthpiece, in one of the sloping top walls of the gable top carton.

U.S. Pat. No. 4,214,675 issued to Schmit on Jul. 29, 1980 discloses one approach which has been taken to dispense products such as wines or other alcoholic beverages wherein it is desirable to prevent the passage of air into the container once the dispensing process has been initiated. Schmit discloses a liquid-containing pouch sealed within a carton. The pouch has a spout connected thereto which projects through a hole in the carton and which is secured to the carton by means of a flange and sleeve arrangement, said flange and said sleeve engaging one another by means of a friction fit. The spout includes a piercing means which is moved axially to rupture the pouch. Liquid to be dispensed passes from the pouch through the spout without coming in contact with the cut edge of the aperture in the paperboard carton. As the liquid is dispensed, the pouch collapses. A valve in the spout forms an airlock to restrict the passage of air into the pouch during and after dispensing of liquids therefrom. This package is both difficult to manufacture and expensive.

Another container which does not include a pouch, but which does include a pouring spout is disclosed in U.S. Pat. No. 4,483,464 issued to Nomura on Nov. 20, 1984. Nomura discloses a container body having a hole of desired size in one of the sloping panels of the gable top, the inner surface of which is coated with a thermoadhesive plastic film or an aluminum foil laminated with such a film. A pouring spout body having an inner spout with a pouring channel and an air inlet is adhered over the aperture in the carton wall to the outermost surface of the carton by means of an integral flange. A cap is placed over the upper end of the pouring spout body. The pouring spout includes a blade for tearing the film adhered over the aperture in the container body to dispense the liquid contents of the container. Once opened, the cut edges of the aperture in the carton wall are exposed to the liquid contents of the carton. In the case of a paperboard carton coated with a liquid impermeable coating on its innermost and outermost surfaces the cut edges of the aperture which are exposed by puncture of the sealing membrane tend to wick the liquid contents of the package into the paper, thereby destroying the integrity of the carton wall in the area where the spout is joined to its surface as well as creating an unpleasant physical appearance about the spout.

Still another sealed gable top carton having a mouthpiece of one piece construction is disclosed in U.S. Pat. No. 4,669,640 issued to Ando et al. on Jun. 2, 1987. Ando et al. disclose a gable top carton comprised of paperboard and having an aperture cut in one of the sloping panels of the uppermost surface of the carton. Closing the aperture is a plastic mouthpiece of one piece construction. The majority of the embodiments disclosed in Ando et al. employ a flange located opposite a multiplicity of retainer lugs along the tubular passageway in the mouthpiece. In most of the disclosed embodiments the mouthpiece is inserted from the innermost surface of the carton until the retaining lugs snap through the aperture and secure it in position for sealing. The flange located on the innermost surface of the carton wall is thereafter fused in liquid tight engagement to the edge portion of the wall around the aperture. The liquid contents of the carton pass through the tubular orifice in the one piece mouthpiece without coming in contact with the cut edges of the aperture. However, any liquid which comes in contact with the exterior of the carton, e.g., due to manufacturing wash down operations or due to condensation effects caused by temperature changes, wicks into the exposed cut edges around the aperture resulting in both poor appearance and structural degradation of the carton wall in the area of the mouth piece.

Ando et al. further disclose, in FIGS. 25 through 27, a mouthpiece embodiment which includes a flange which is sealed to the external surface of the gable top side wall around the aperture used for dispensing the liquid contents of the carton. However, this embodiment employs no innermost flange or liquid tight seal and so allows exposure of the cut edges of the aperture to the liquid contents of the carton both prior to and after opening of the carton by the consumer. Even if one were to provide an innermost moisture-barrier membrane to protect the cut edges of the aperture prior to opening of the carton by the consumer, once the moisture-barrier membrane is opened by the consumer the cut edges of the aperture would be immediately exposed to the liquid contents of the carton during the dispensing operation.

The wicking problems of the aforementioned Ando et al. carton embodiment are even further aggravated due to the manner in which the mouthpiece is opened. In particular, the mouthpiece is opened by partially separating the sealed flange from the outermost surface of the carton wall and folding it back along a hinge line in the mouthpiece. This separation of the sealed flange from the exterior surface of the carton wall substrate tends to cause portions of the moisture resistant outermost layer of the carton wall to delaminate from the paperboard during the opening process and remain secured to the mouthpiece flange after it is opened. Raw edges of the paperboard are thereby exposed in areas over which the liquid being dispensed must pass, thereby further aggravating the wicking problem in the area surrounding the aperture in the carton wall.

There have been prior art attempts to solve the aforementioned wicking problems by applying pairs of polymeric layers to opposite surfaces of a carton board wall over an aperture in the carton board wall, joining the polymeric layers coinciding with the aperture to one another through the aperture and thereafter punching a hole through the central portion of the joined layers. U.S. Pat. No. 4,397,401 issued to Ueno et al. on Aug. 9, 1983 is representative of such an approach. These techniques are usually difficult to reliably execute. Perhaps more importantly, however, they do not provide an easily reclosable pouring spout suitable for shaking the product prior to dispensing or for mess-free dispensing of liquid products such as milk, juice or liquid laundry additives from cartons comprised of paperboard laminate.

A solution to many of the aforementioned prior art problems is disclosed in the commonly assigned co-pending U.S. Patent Application of Donald E. Jones and Michael T. Brown entitled "MOISTURE IMPERVIOUS CARTON HAVING ONE PIECE POURING SPOUT SEALED TO INNERMOST AND OUTERMOST SURFACES, Ser. No. 196,418, filed on May 20, 1988. The aforementioned co-pending patent application of Jones et al. discloses a liquid containing paperboard laminate carton including a one-piece plastic spout having a pair of opposing flanges sealed about an aperture in one of the carton walls to both the innermost and outermost surfaces of the carton wall. The double flange configuration not only forms a mechanically positive interlock between the plastic spout and the carton wall, but also isolates the cut edges of the aperture in the carton wall from exposure to liquid either from within the container or from the environment through which the carton must pass from the point of manufacture until it is ready for disposal after its contents have been consumed. The spout, which is preformed so as to include one of the flanges, preferably includes a liquid passageway having a membrane type seal across its discharge orifice to provide evidence of tampering. A resealable closure member such as a screw cap or a snap-on closure is preferably held in place by means of a mating ring or groove on the spout. The cross-sectional area and configuration of the liquid passageway and discharge orifice of the spout are preferably designed to prevent complete blockage by liquid when the package contents are being dispensed during a normal dispensing cycle, i.e., when the package is not being held completely upside down.

While method and apparatus for either sequential or simultaneous sealing of both flanges of the spout of Jones et al. are disclosed in the aforementioned commonly assigned co-pending U.S. Patent Application, considerable care must be exercised to provide needed support for each flange to effect simultaneous sealing of each flange to the surface of the carton board adjacent thereto. This is due in large part to the fact that the flange sealing surfaces on opposite surfaces of the carton board do not completely coincide with one another when a spout configuration such as that disclosed in the Drawing Figures of the commonly assigned, co-pending U.S. Patent Application of Jones et al. is employed.

OBJECTS OF THE INVENTION

Accordingly, it is an object of the present invention to provide a liquid containing paperboard laminate carton including an improved one-piece plastic pour spout having a pair of opposing flanges sealed about an aperture in one of the carton walls to both the innermost and the outermost surfaces of the carton wall.

It is another object of the present invention to provide method and apparatus for more easily and reliably securing the innermost and outermost flanges on said improved one-piece plastic pour spout in sealed liquid-tight relation to the innermost and outermost surfaces, respectively, of the carton wall in a single step.

DISCLOSURE OF THE INVENTION

In a particularly preferred embodiment the present invention comprises a gable top paperboard laminate carton for containing a liquid product such as milk, juice, laundry additive, etc. The innermost and outermost surfaces of the carton typically are coated with a polymer which is both liquid impermeable and preferably heat sealable.

One of the tapered side walls at the uppermost end of the carton preferably includes an aperture which is fitted with an improved one-piece plastic spout of the present invention. The spout includes a liquid passageway which preferably employs a membrane type seal across its discharge orifice to provide evidence of tampering and to prevent pilferage or contamination. The spout also preferably includes resealable closure means, such as a screw cap or snap top cap held in place by a complementary ring and groove arrangement.

In a particularly preferred embodiment, the spout of the present invention is molded from plastic and, prior to installation, includes an uppermost preformed flange which contacts the outermost surface of the carton about an aperture in the carton wall. A truncated skirt having a maximum cross-section small enough to pass through the aperture in the carton wall depends from the lowermost surface of the uppermost preformed flange. While it is not a requirement that all portions of the truncated skirt be no larger than the aperture in the carton wall, the size relationship between the skirt and the aperture in the carton wall must be such that the skirt can be passed through the aperture without permanently damaging either the skirt or the carton wall containing the aperture. For example, the maximum cross-section of the skirt may be slightly larger than that of the aperture, provided it is resilient and will undergo a degree of deflection so as to "snap" through the aperture in the carton wall. This type of fit may be advantageous where the spout insertion step is performed before the carton reaches the swaging and sealing station, since the spout will readily be retained in proper position within the aperture in the carton wall until the carton actually reaches the swaging and sealing station.

A lowermost flange is preferably formed from the truncated skirt which depends from the lowermost surface of the uppermost preformed flange after the skirt has been inserted from the outside of the carton through the aperture in the carton wall by deforming the truncated skirt portion of the spout via the application of pressure, optionally in conjunction with heat. Prior to formation of the lowermost flange, the liquid passageway of the improved spout preferably exhibits two distinct cross-sections. The first and smaller cross-section exists in that portion of the spout located between the preformed flange and the discharge orifice. The other larger cross-section comprises the truncated skirt which exhibits a minimum cross-section substantially equal to or greater than the maximum cross-section of the exterior portion of the spout located above the preformed flange. If a resealable closure means is preassembled onto the spout prior to affixing the spout to the carton wall, then the minimum cross-section of the skirt is also preferably substantially equal to or greater than the maximum cross-section of the resealable closure means. As pointed out in the preceding paragraphs, the maximum cross-section of the truncated skirt must be small enough to pass through the aperture in the carton wall without permanently damaging either the skirt or the carton wall containing the aperture, yet large enough to coincide with at least a portion of the preformed flange and to fully cover the cut aperture in the carton wall after swaging. Finally, the uppermost or outermost preformed flange must likewise be of larger cross-section than the exterior portion of the spout and, if employed, the maximum cross-section of any resealable closure means which is preassembled to the spout.

Because the lowermost or innermost flange which is formed in place by swaging the truncated skirt exhibits a minimum cross-section which is greater than the maximum cross-section of the exterior portion of the spout and, if applicable, the maximum cross-section of any resealable closure means preassembled thereto, heat and pressure can be simultaneously applied to both the exterior and interior flanges in an area where the flanges coincide with one another without subjecting any other portions of the spout and/or resealable closure means to pressure. This permits easy and reliable simultaneous sealing of both flanges to the opposing surfaces of the carton wall in a single step.

In an alternative embodiment of the present invention, the plastic spout includes a preformed innermost flange having a truncated skirt extending upwardly and outwardly from its uppermost surface. The spout is inserted from the innermost surface of the carton, and the outwardly oriented truncated skirt is deformed by the application of pressure, optionally in conjunction with heat, to form an outermost flange adjacent the outermost surface of the carton wall. As with the other spout embodiments described herein, the coinciding portions of the innermost and outermost flanges can thereafter be simultaneously sealed to the adjacent surface of the carton wall without subjecting any other portions of the spout and/or resealable closure means to pressure.

Regardless of which improved spout configuration of the present invention is employed, the resultant double flange forms a mechanically positive interlock between the plastic spout and the carton wall. Even more importantly, the double flange/double seal combination isolates the cut edges of the aperture in the carton from exposure to liquid either from within the container or from the environment through which the carton must pass from the point of manufacture until it is ready for disposal after its contents have been consumed.

Furthermore, because both flanges may be simultaneously supported, many different types of sealing operations, e.g., heat sealing, ultrasonics, etc., may be employed to effect deformation of the innermost skirt and simultaneous or, if desired, sequential sealing of the opposed flanges to the opposing surfaces of the carton board.

The present invention also has beneficial application to structures besides laminated paperboard cartons which are liquid impervious on both surfaces. For example, package structures of the bag-in-box type, i.e., a structure wherein a flexible polymeric bag is used to house a liquid within a paperboard carton, may beneficially practice the present invention. For example, the polymeric bag containing the liquid may be secured to both the innermost flange of the spout and the innermost surface of the carton about the aperture in the carton wall to provide a liquid tight joint protecting the carton board from exposure to any of the liquid contained within the bag. If the exterior surface of the carton is liquid impervious, the exterior flange of the spout may also be sealed to the liquid impervious exterior layer. The resultant bag-in-box package yields substantially the same benefits as can be provided with a laminated carton board having liquid impervious exterior and interior layers.

In still other embodiments of the present invention the opposing flanges of the spout can be simultaneously sealed to the opposing surfaces of a flexible polymeric film pouch to provide a flexible liquid containing package having an attached pour spout for mess-free dispensing of its contents. Disposable packages of the latter type are particularly useful for refilling non-disposable rigid or semi-rigid dispensing containers such as those used for liquid laundry detergents, fabric softeners, bleaches, etc. The flexible film pouches can be collapsed to a very small volume once their liquid contents have been transferred or consumed to minimize the volume of solid waste to be disposed of.

BRIEF DESCRIPTION OF THE DRAWINGS

While the specification concludes with claims particularly i pointing out and distinctly claiming the present invention, it is believed the present invention will be better understood from the following description in conjunction with the accompanying drawings in which:

DETAILED DISCLOSURE OF THE INVENTION
ONE-PIECE PLASTIC POUR SPOUT

Figure 1:
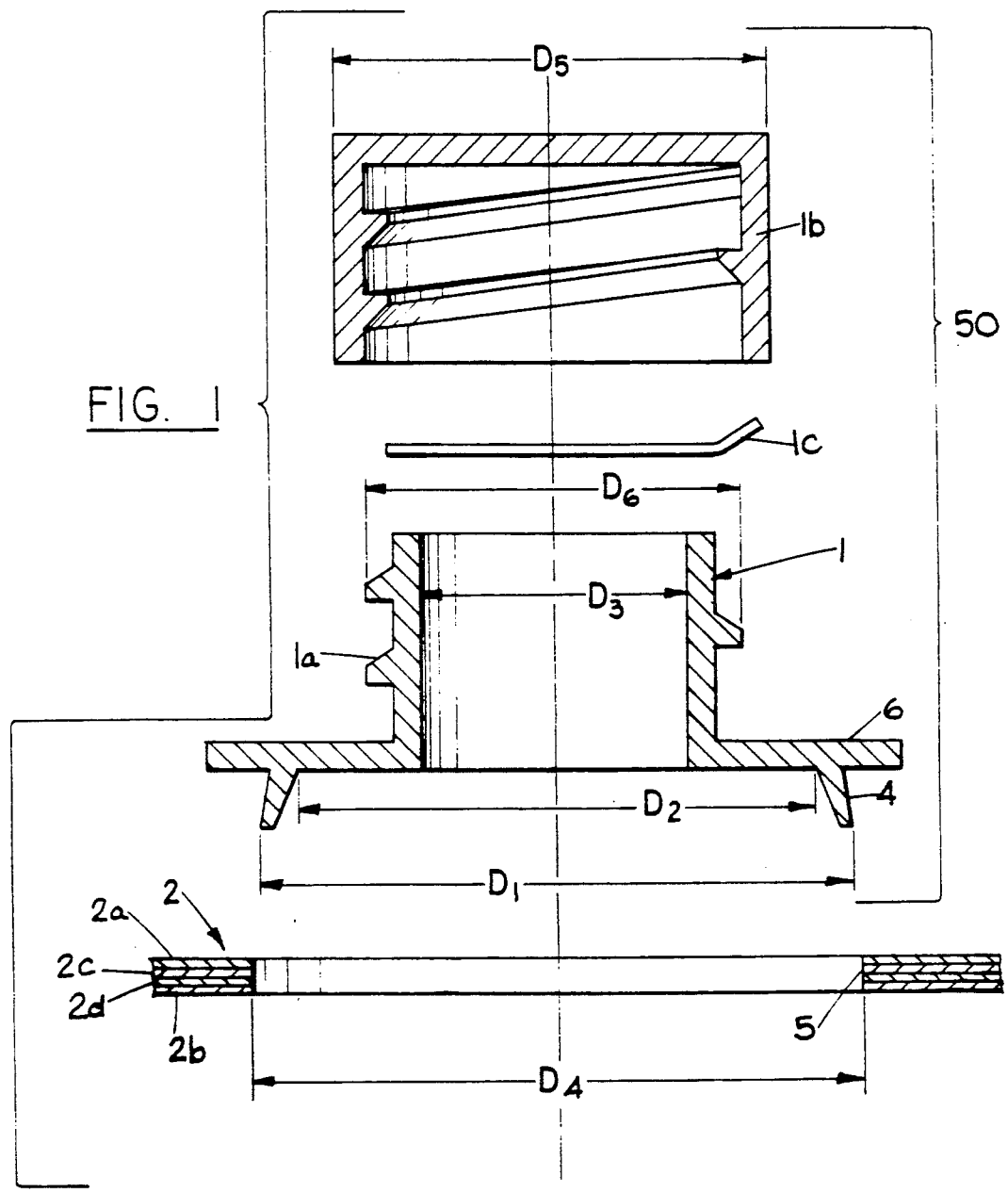
FIG. 1 is a greatly enlarged, simplified, exploded view of an apertured carton wall, a one-piece pouring spout, a tamper evident sealing membrane and a resealable threaded closure means of the present invention.
Figure 11:
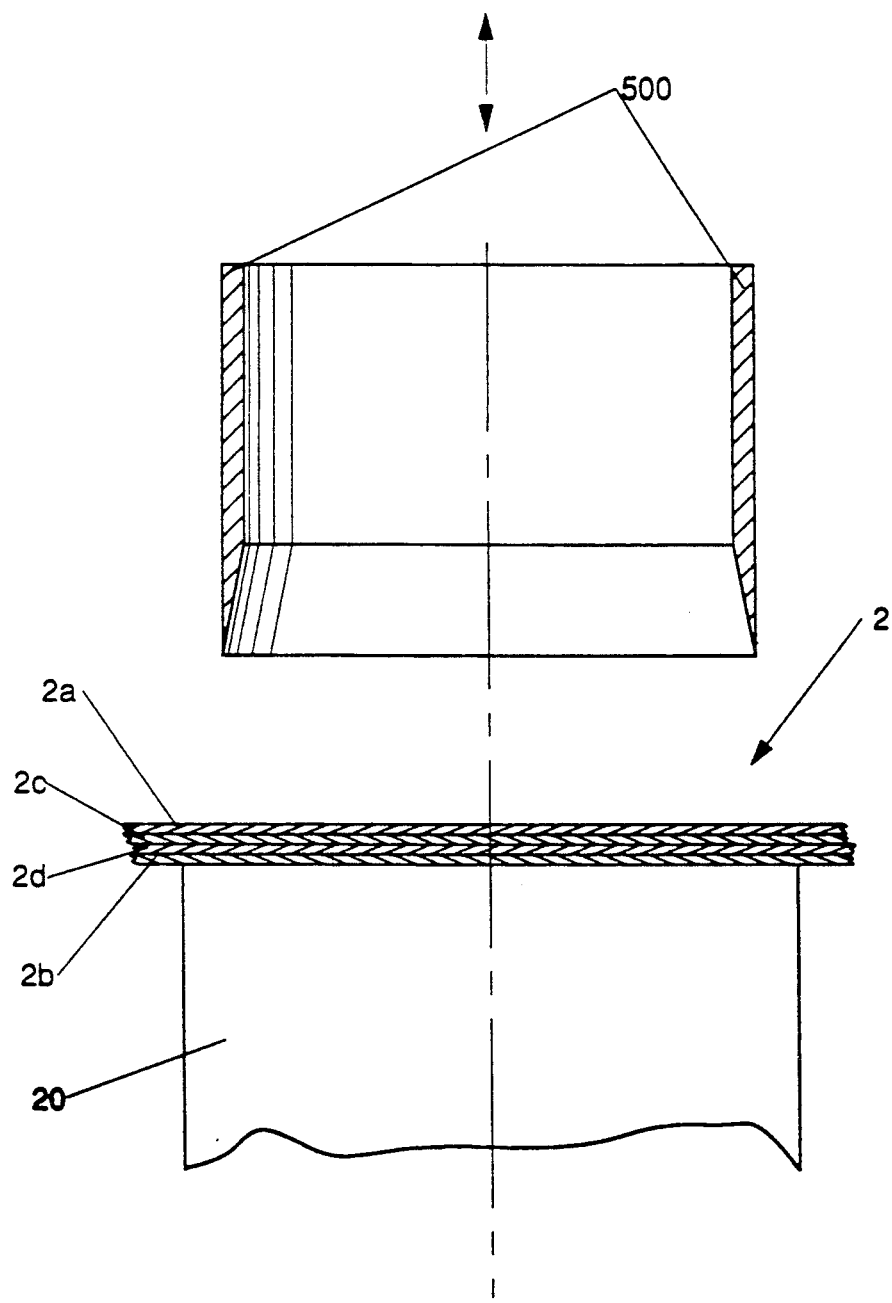
FIG. 11 is a simplified schematic cross-sectional illustration of a means for cutting a hole of predetermined cross-section in one of the walls of a package of the present invention.

The present invention, in a particularly preferred embodiment, comprises a one-piece pouring spout that can be attached to a carton board package. While the present description is in the context of a cylindrical spout, it will be understood that the particular cross-sectional configuration of the spout, as measured perpendicular to its liquid passageway, is non-critical, e.g., it may be square, diamond-shaped, oval, etc. The spout 1 shown in FIG. 1, which has a centrally located liquid passageway, is intended to be sealed simultaneously to both the inside and outside surfaces of the carton board 2, thereby forming a pair of liquid-tight seals which protect the cut edges of the hole 5 in the carton board wall from exposure to liquid. The hole 5 in the carton board wall 2 may be provided by many different means known in the art. For example, the cutting means 500 may comprise a simple tubular shaped member, as schematically shown in the cross-section of FIG. 11. The cutting means 500 may be urged against the carton wall 2 while the carton wall is supported on a hard surfaced anvil 20, which may also be used during the swaging and sealing processes. The cutting means is thereafter refracted once the hole has been cut. FIG. 1 is an exploded cross-sectional schematic showing a particularly preferred spout 1, carton wall 2, sealing membrane 1c and resealable closure 1b. The spout 1 has a threaded portion 1a, a preformed outer flange 6, and a truncated skirt 4 depending from the preformed flange.

A mating threaded cap 1b and a tamper-evident pull-tab liner 1c, which is normally heat sealed across the discharge orifice of the spout, are preferably preassembled to the spout 1 to form a fitment 50 which is attached as an assembly to the laminate carton board 2. If desired, the spout 1 could be provided with an external ring (not shown) in lieu of the external thread 1a shown in FIG. 1. In the latter case, the internal surface of the closure means, e.g., cap 1b, could be provided with a mating groove (also not shown) to permit engaging and disengaging said cap and said spout with one another. Also, if desired, the positions of the mating ring and groove may be interchanged with one another, i.e., an external groove could be provided on the spout 1 and a mating ring could be provided on the internal surface of the cap 1b.

The laminate carton board 2 has an outermost layer 2a comprised of a polymeric material (typically low density polyethylene, hereinafter referred to as LDPE) and an innermost layer 2b comprised of a polymeric material (typically LDPE, a blend of LDPE and Ionomer, glycol-modified polyethylene terephthalate, hereinafter referred to as PET-G, or polyethylene terephthalate, hereinafter referred to as PET) and includes an aperture 5 which is large enough for the preformed truncated skirt 4 of the spout to pass through without causing any permanent damage to either the skirt or the carton wall containing the aperture. In the case of a cylindrical spout and cylindrical hole, the diameter $D_4$ of cut hole 5 is preferably slightly greater than the maximum diameter $D_1$ of truncated skirt 4 of spout 1 prior to any expansion of the skirt. Embedded between the innermost and outermost layers of carton board 2 there is normally provided a layer of cellulose carton board 2c and a barrier layer 2d typically comprised of a material such as foil, PET-G or ethylene vinyl alcohol, hereinafter referred to as EvOH. As will be explained in greater detail hereinafter, the truncated spout skirt 4 is expanded to form an interior flange and is sealed in liquid tight relation to the innermost layer 2b while the outer flange 6 is simultaneously sealed in liquid tight relation to the outermost layer 2a of carton board 2.

As pointed out earlier, cartons of the type generally disclosed herein preferably have substantially liquid impervious layer 2b and 2a on their innermost and outermost surfaces, respectively. The innermost and outermost layers each typically exhibit a thickness in the range of about 0.0008 to about 0.0014 inches. The intermediate paper board layer 2c has a typical thickness in the range of about 0.017 to about 0.024 inches. The barrier layer 2d typically exhibits a thickness in the range of about 0.000285 to about 0.00035 inches if comprised of aluminum foil and a thickness in range of about 0.006 to about 0.017 inches if comprised of a polymeric material such as PET-G or EvOH.

If a polymeric barrier layer 2d is employed in lieu of aluminum foil, another layer (not shown) is preferably sandwiched between the paperboard layer 2c and the innermost layer 2b to provide light blockage for products which are subject to degradation by light. This additional layer is typically comprised of pigmented LDPE having a thickness between about 0.0008 and about 0.0015 inches.

PROCESS DESCRIPTION

Attachment of the fitment shown in the exploded view of FIG. 1 to the carton board wall 2 is schematically depicted in Drawing FIGS. 2-5. If desired, the ultrasonic horn 10 shown in FIG. 3 can be employed as the means for inserting the truncated skirt 4 extending from the preformed flange 6 of the one piece pouring spout 1 through the cut hole 5 in the wall 2 of the carton as well as the means for bringing the preformed flange into contacting relation with the carton wall about the periphery of the cut hole.

Figure 2:
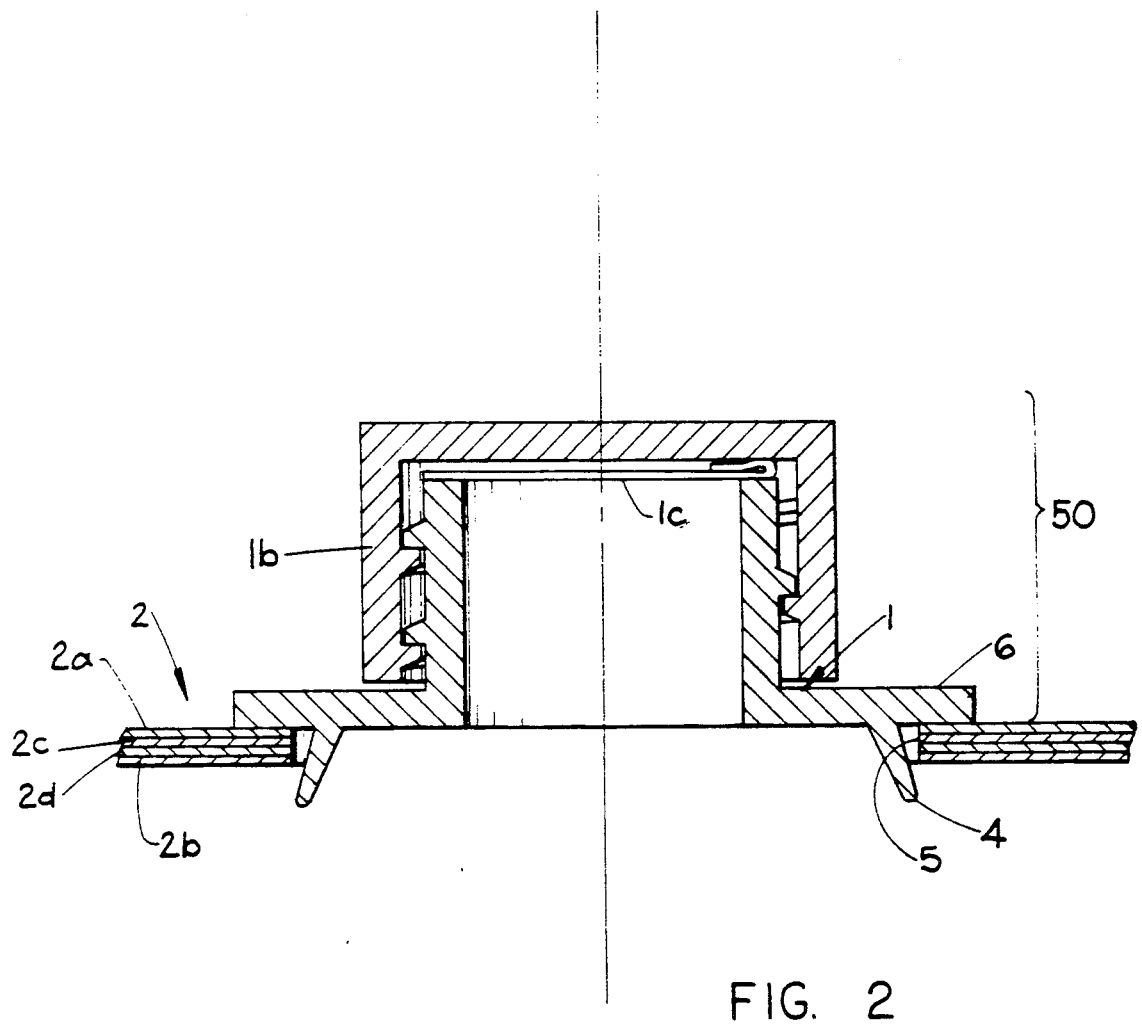
FIG. 2 is a simplified cross-sectional schematic illustration showing the assembled fitment comprising a one-piece pouring spout, the tamper evident sealing membrane and the resealable threaded closure means after they have been assembled and inserted into an apertured carton wall.

FIG. 2 shows a pour spout 1 with a preassembled cap 1b and sealing membrane 1c attached after the pour spout has been inserted into the cut aperture 5 in the carton board wall 2.

Figure 4:
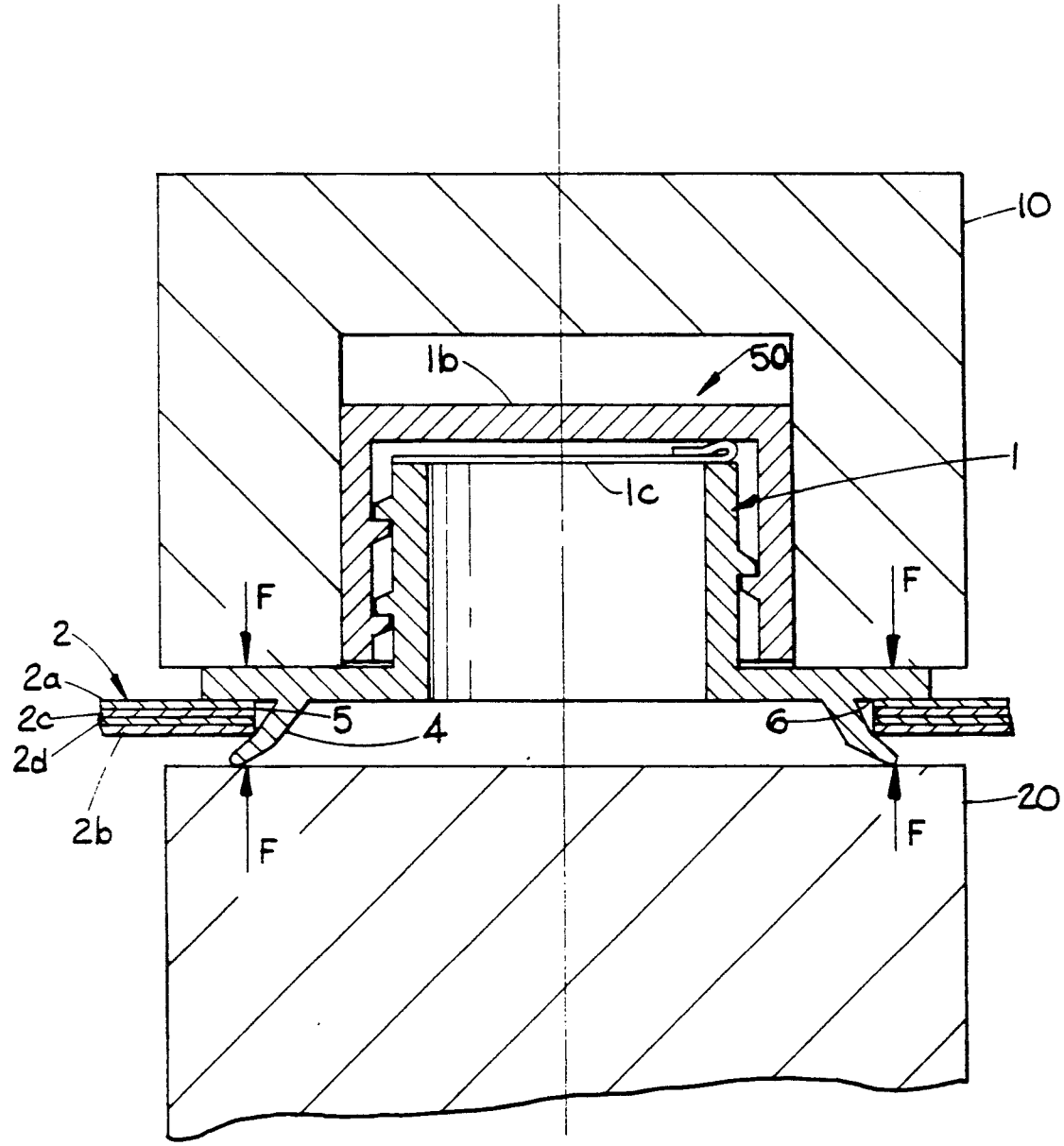
FIG. 4 is a view of the fitment and carton wall shown in FIG. 3 as opposing forces "F" are being applied to the opposing flange and skirt portions of the spout by the ultrasonic horn and anvil.

The outside diameter $D_1$ of the truncated spout skirt 4 shown in FIGS. 1 and 2 is preferably slightly smaller, most preferably at least about 0.005 inches to 0.010 inches smaller, than the aperture diameter $D_4$ to facilitate easy insertion of the spout skirt 4 through the aperture 5. The spout skirt 4 is preferably angled outwardly (truncated) from the centerline of the spout 1 in order to assure that upon application of opposed compressive forces "F" by an ultrasonic horn 10 and anvil 20, as shown in FIGS. 4 and 5, the skirt material swages outwardly to encapsulate the cut edges of the carton board material about the aperture 5.

Upon complete insertion of the spout skirt 4 into the aperture 5, as shown in FIG. 2, the bottom of the spout's outermost preformed flange 6 rests upon the outside of the carton board 2. In order for the horn 10 and anvil 20 to cause sufficient compressive forces "F" on the truncated skirt 4, the skirt's root diameter $D_2$, i.e., its minimum cross-section, is preferably substantially equal to or greater than the maximum outside diameter $D_6$ of the spout 1 if no resealable closure 1b is applied or intended. If a resealable closure means 1b is to be preassembled to the spout, then the skirt's root diameter $D_2$ is preferably substantially equal to or greater than the maximum outside diameter $D_5$ of the resealable closure means 1b. If the root diameter $D_2$ of the truncated skirt 4 is substantially smaller than the maximum diameter $D_6$ of the spout (i.e., the maximum cross-section of the exterior portion of the spout located above the preformed flange 6 where no resealable closure means 1b is employed) or the maximum diameter $D_5$ of the resealable closure means 1b (i.e., the maximum cross-section of the exterior portion of the fitment located above the preformed flange 6 where such an element is preassembled to the spout), then the opposing compressive forces "F" applied by the horn 10 and anvil 20 are more prone to deform spout's outermost flange 6 than to outwardly swage the truncated skirt 4, as generally shown in FIGS. 4 and 5.

Figure 3:
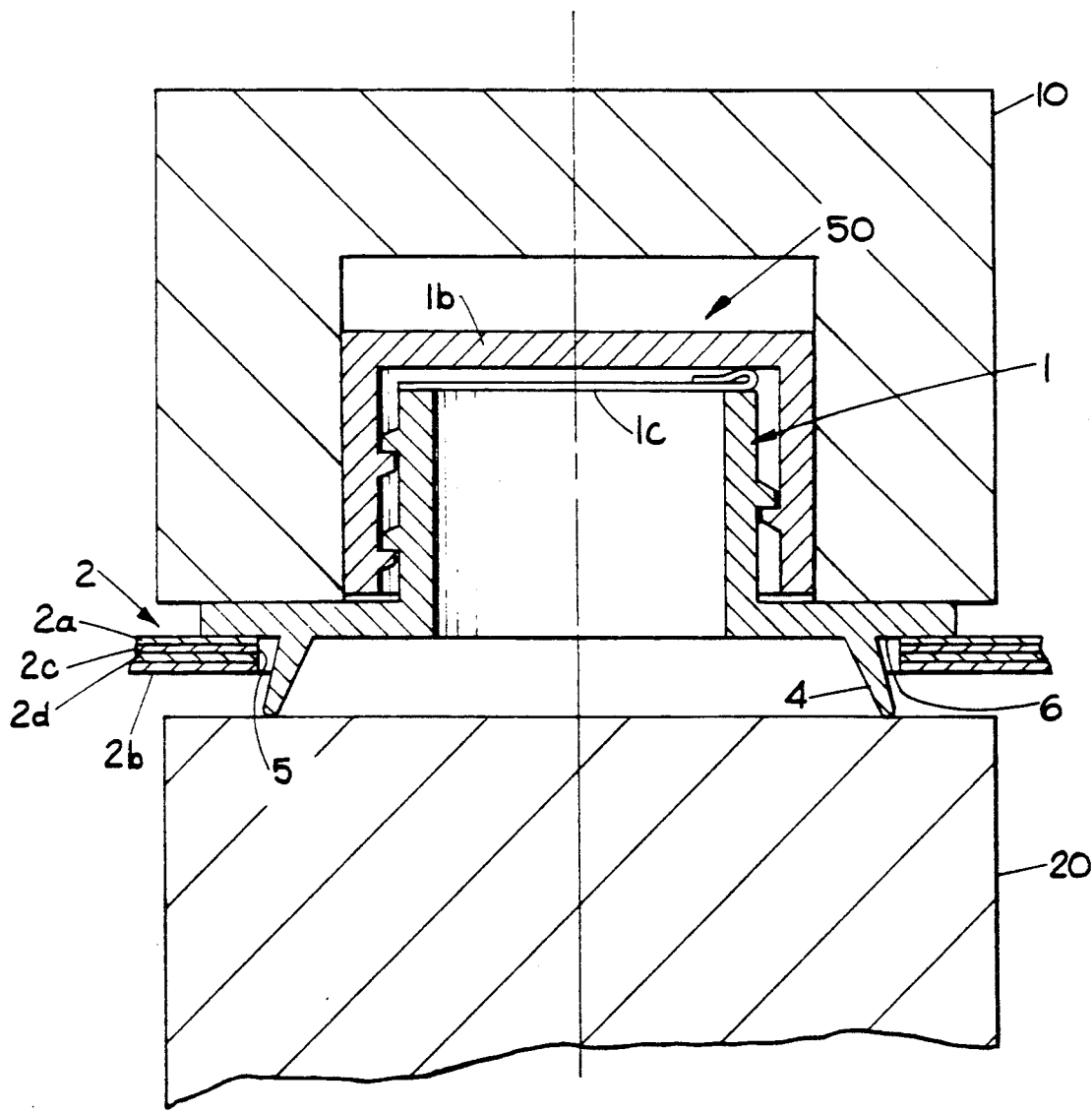
FIG. 3 is a view of the fitment and carton wall shown in FIG. 2 after an ultrasonic horn has contacted the outermost preformed flange of the spout and an anvil member has contacted the lowermost end of the truncated skirt depending from the preformed flange.

FIG. 3 shows a preferred anvil 20 which, in the case of an ultrasonic sealing system, preferably comprises a flat solid backup material, preferably steel, contacting the lowermost portion of the truncated spout skirt 4 without lifting the skirt back out of the aperture 5. The swaging process is preferably initiated by placing the ultrasonic horn 10, which surrounds the spout's cap 1b and which need not be vibrating during this portion of the operation, in contact with the uppermost surface of the outermost flange 6 of spout 1 and applying opposing compressive forces "F" between the horn 10 and anvil 20, as generally shown in FIG. 4. If desired, the anvil 20 may be heated during the skirt swaging process.

Figure 5:
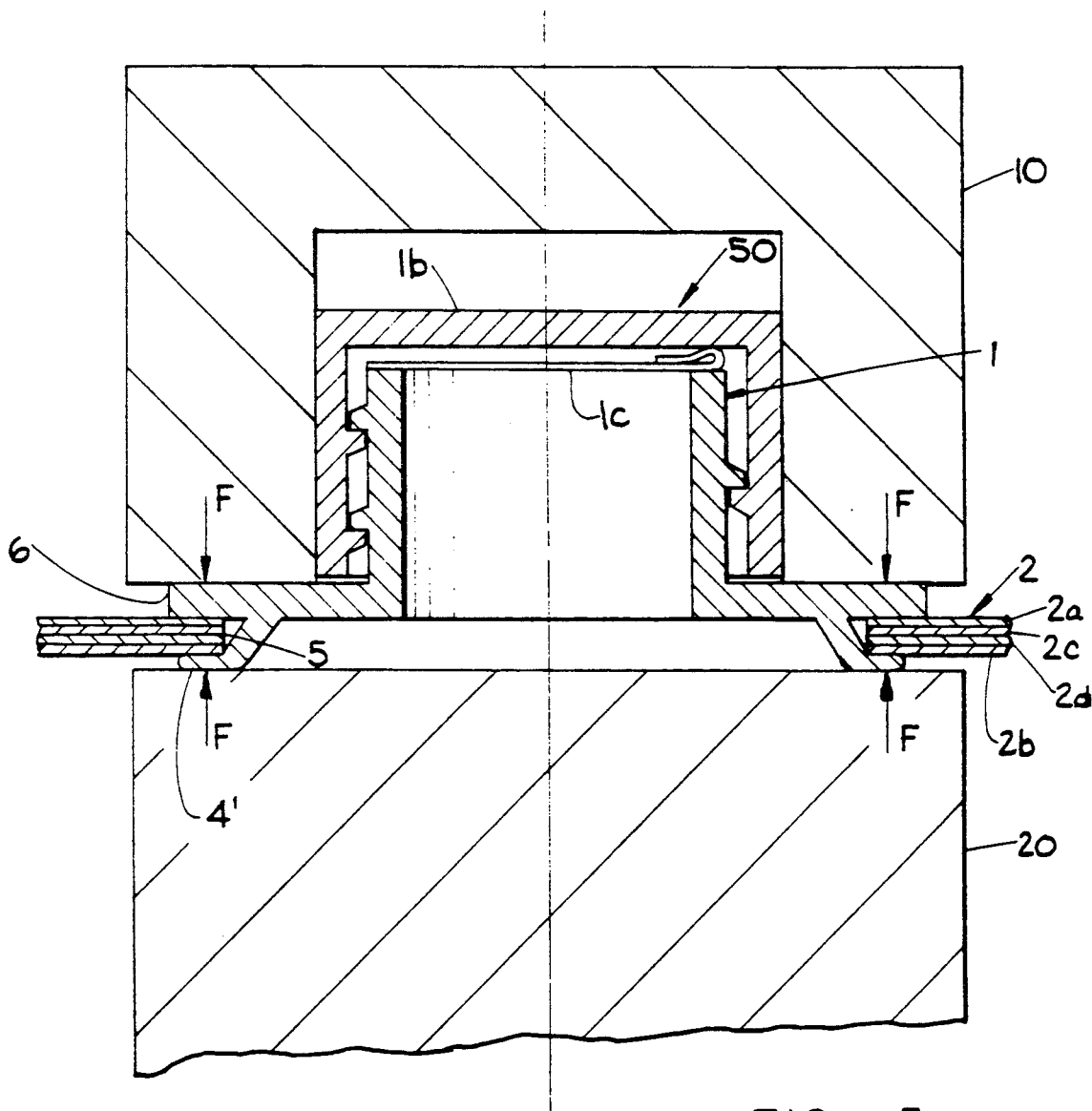
FIG. 5 is a view of the fitment and carton wall shown in FIG. 4 after the innermost skirt has been completely deformed to an outwardly horizontal position by means of the ultrasonic horn and the opposing anvil.
Figure 6:
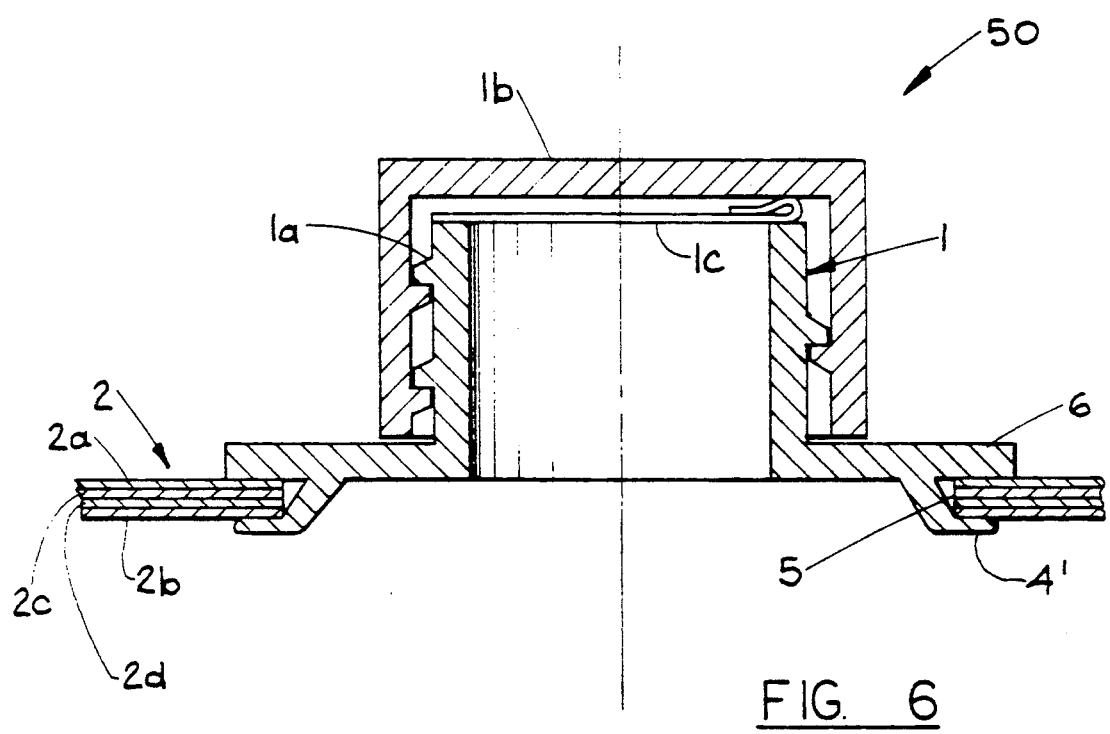
FIG. 6 is a view of the fitment and carton wall shown in FIG. 5 after the opposing flanges of the fitment have been sealingly secured to the opposing surfaces of the laminate carton board wall about the periphery of the aperture.

After the spout skirt 4 has been fully swaged so as to form an innermost flange 4', as shown in FIG. 5, and while still subject to opposing compressive forces "F" the ultrasonic system is energized to convert high frequency (in the range of about 20 kilohertz) electrical energy to a high frequency mechanical energy, thereby causing the ultrasonic horn 10 to vibrate at a frequency of about 20 kilohertz. The high frequency mechanical energy in the form of the vibrating ultrasonic horn 10 simultaneously heats outermost polymeric layers 2a and 2b of carton board 2 and the adjacent portions of outermost flange 6 and innermost swaged flange 4', as generally shown in FIG. 5. Heating these adjacent materials to a semi-molten state allows them to fuse to one another upon cooling, i.e., the lowermost surface of outermost flange 6 fuses to the uppermost layer 2a of carton board 2 while the uppermost surface of innermost flange 4' fuses to the innermost layer 2b of carton board 2. Continuous fusing of the materials to one another about the periphery of the opposing flanges provides a liquid-tight seal which protects layers 2c and 2d of the carton board 2 about the periphery of cut aperture 5.

Because uniform pressure can be easily and reliably simultaneously applied directly to the coinciding portions of outermost flange 6 and innermost flange 4' with the improved spouts of the present invention, it is possible to easily and reliably simultaneously seal each flange to the adjacent surface of the carton board without subjecting any other portions of the fitment to pressure. When thermoplastic materials, such as high density polyethylene (HDPE) or low density polyethylene (LDPE) are employed for the spout 1 and outermost layers 2a and 2b of the carton board, the time required to effect simultaneous sealing of both flanges, each having an initial thickness in the range of about 0.012 and about 0.015 inches, to the opposing surfaces of the carton board is typically on the order of about 0.20 to about 0.35 seconds. These results are normally obtainable using an ultrasonics system comprising a Sonics & Materials 20 Kilohertz Ultrasonic Welder No. EM 1500, as available from Sonics & Materials, of Danbury, Conn. and an anvil contact pressure of about 440 pounds per square inch, based on the contact area between the coinciding portions of flanges 6 and 4' with horn 10 and anvil 20, respectively. As will be appreciated by those skilled in the art, the precise configuration of the ultrasonic horn 10 and anvil 20 are noncritical, provided the horn and anvil coincide at least over those portions of innermost flange 4' and outermost flange 6 which coincide with one another. As will also be appreciated by those skilled in the art, the ultrasonic horn 10 may be energized after swaging of spout skirt 4 to form interior flange 4' or, alternatively, the ultrasonic horn 10 may be energized throughout the swaging and sealing process.

While the particular polymeric materials chosen for spout 1 and outermost carton board layers 2a and 2b may differ from one another, best bonding results are generally obtained when materials which are similar to one another are employed, i.e., fusing generally occurs more readily between polymeric materials which are identical to or similar to one another than between polymeric materials which differ widely from one another.

If desired, a simple heat sealing operation may be employed rather than ultrasonics to effect the simultaneous flange sealing operations schematically shown in FIGS. 4–5. In the latter case the internal skirt swaging and sealing anvil employed in lieu of ultrasonic anvil 20 and the outside flange sealing anvil employed in lieu of ultrasonic horn 10 are both preferably heated to a temperature in the range of about 350°–400° F. However, in the event a heat sealing system is employed rather than ultrasonics, care must be taken with respect to the uppermost heated anvil used in lieu of ultrasonic horn 10 to insulate or otherwise isolate the resealable closure means 1b and/or the external surface of the spout 1 from the heated upper anvil to avoid degradation thereof during the swaging and sealing process.

Required sealing times using a heated anvil system are, in general, slightly longer than for the ultrasonic sealing system. Typical sealing times for a heated anvil sealing system when spouts 1 and carton board 2 comparable to those employed with the ultrasonics sealing system described earlier herein are in the range of about 1.4 seconds.

Alternative Package Forms

Figure 7:
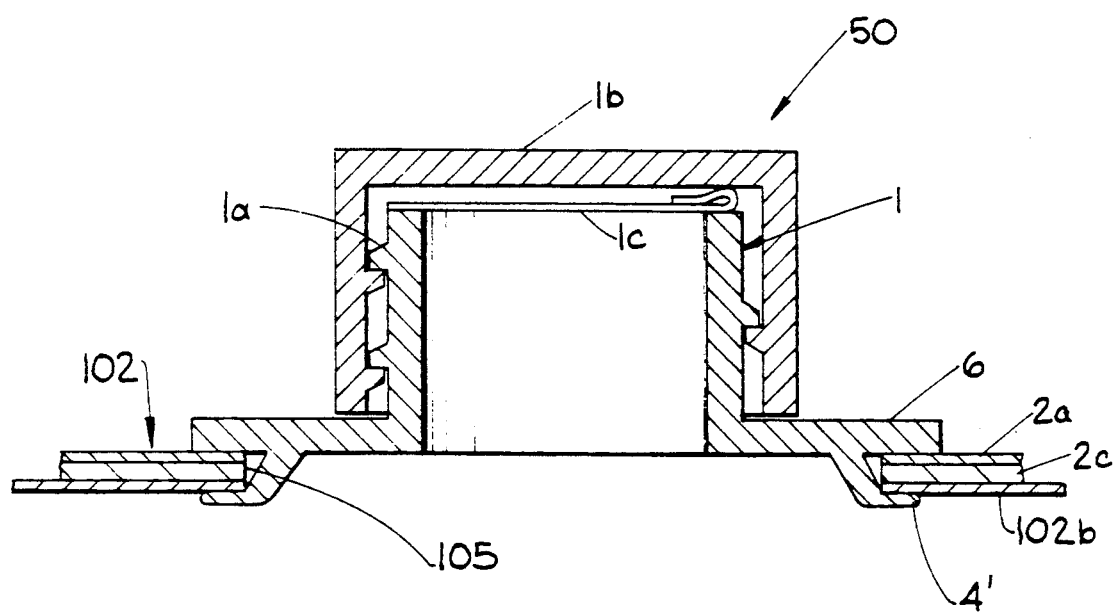
FIG. 7 is a view of an alternative package of the present invention generally similar to that shown in FIGS. 1-6, but wherein the innermost flange of the spout has been sealed to a flexible polymeric bag which lines the interior of the package and the other surface of the polymeric bag has been sealed to the innermost surface of a paperboard layer in the surrounding carton, such as might be employed in a bag-in-box structure.

As will be appreciated by those skilled in the art, the present invention is not limited to moisture impervious cartons comprised exclusively of laminated paperboard. For example, FIG. 7 illustrates an alternative embodiment of the present invention wherein a spout 1 identical to that shown in FIG. 1 is secured to a bag-in-box package wherein the carton board 102 of which the exterior package is comprised includes only an outermost moisture impervious layer 2a and a backup cellulosic layer 2c. In this embodiment, a flexible polymeric bag or liner 102b completely lines the interior of the carton.

The material comprising liner 102b is preferably a thermoplastic such that performing substantially the same operations illustrated in FIGS. 4–5 on the package shown in FIG. 7 will cause fusing of the lowermost surface of outermost flange 6 to outermost layer 2a of carton board 102 as well as simultaneous fusing of liner material 102b to the innermost surface of interior flange 4' and the innermost surface of carton board layer 2c.

This produces a liquid-tight seal about the periphery of the spout 1 which protects all portions of carton board layer 2c from any liquid contained within polymeric liner 102b, while the continuous seal between outermost flange 6 and outermost layer 2a protects carton board layer 2c from any liquid to which the exterior of the package is subjected prior to consumption of its contents.

Figure 8:
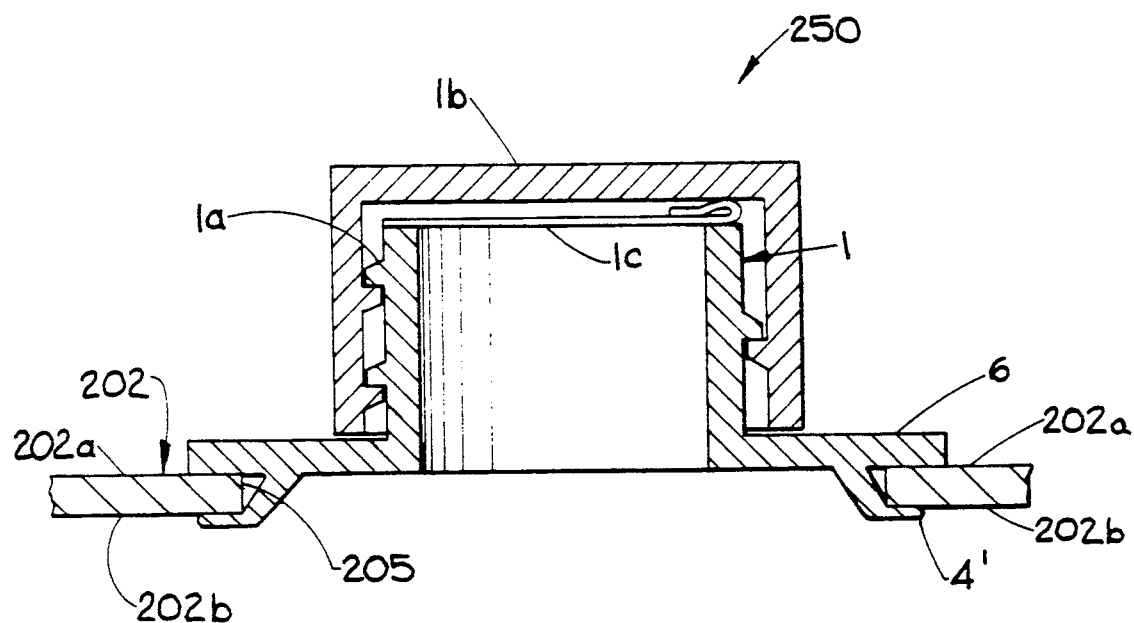
FIG. 8 is a view of still another package of the present invention wherein the opposing flanges of a spout similar to that shown in FIGS. 1-7 have been sealed to the opposing surfaces of a flexible polymeric package.

FIG. 8 shows still another package embodiment of the present invention wherein the coinciding portions of opposing flanges 6 and 4' are simultaneously sealed to the opposing surfaces 202a and 202b, respectively, of a flexible polymeric pouch wall about the periphery of a cut aperture 205.

Figure 9:
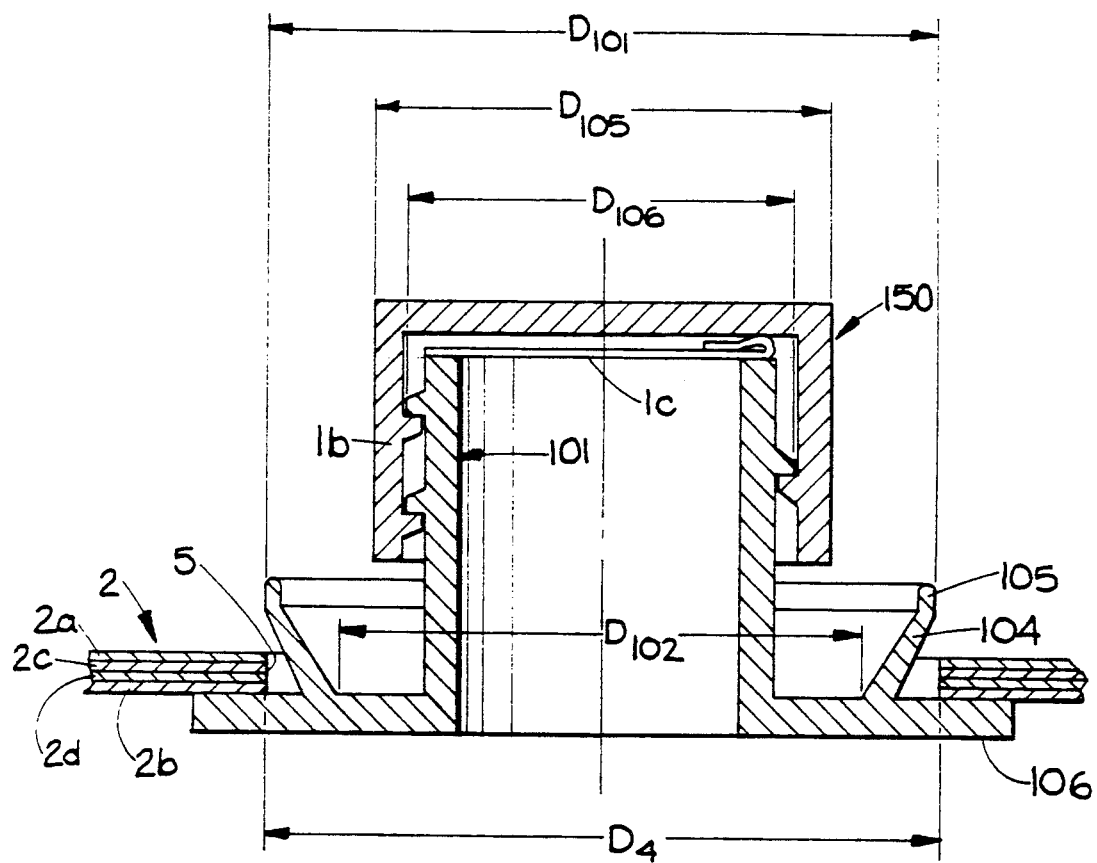
FIG. 9 is a view of an alternative fitment and carton wall of the present invention wherein the fitment is inserted from the interior of the carton and the upwardly and outwardly extending truncated skirt located on the uppermost surface of the preformed interior flange has been "snapped" through the aperture in the carton wall.

FIG. 9 discloses an alternative fitment 150 of the present invention generally similar to fitment 50 shown in FIGS. 1–8 with the exception of spout 101. In particular, the polymeric pour spout 101 shown in FIG. 9 is intended for insertion from the interior of the carton into aperture 5 in carton wall 2. The resealable closure means 1b, tamper-evident seal 1c and carton wall 2 are identical to those employed in the embodiment of FIGS. 1–8. However, polymeric spout 101 employs a preformed interior or lowermost flange 106 rather than a preformed outermost flange. Accordingly, the truncated skirt 104 extends upwardly and outwardly from the uppermost surface of preformed flange 106. While the upwardly oriented truncated skirt 104 may, if desired, be configured identically to truncated skirt 4 on spout 1, truncated skirt 104 includes a lead in chamfer 105 which facilitates snapping the maximum cross-section of the skirt 104 through the slightly smaller cross-section of the aperture 5 in carton wall 2.

As can be seen from FIG. 9, the minimum cross-section of the truncated skirt 104, as reflected by root diameter $D_{102}$, is greater than the maximum external cross-section of the spout 101, as reflected by diameter $D_{106}$, and the maximum external cross-section of the reclosable sealing means 1b, as reflected by diameter $D_{105}$.

Unlike pour spout 1, shown in FIG. 1, the maximum cross-section of upwardly extending truncated skirt 104 of spout 101 corresponds to diameter $D_{101}$ which is slightly greater than the diameter $D_4$ of the aperture 5 in carton wall 2. Accordingly, once the upwardly and outwardly extending truncated skirt 104 of fitment 101 has been snapped through the aperture 5 in the carton wall 2, the fitment will be retained by the carton wall until such time as it is subjected to a swaging and sealing operation generally similar to those shown in FIGS. 3–6.

Figure 10:
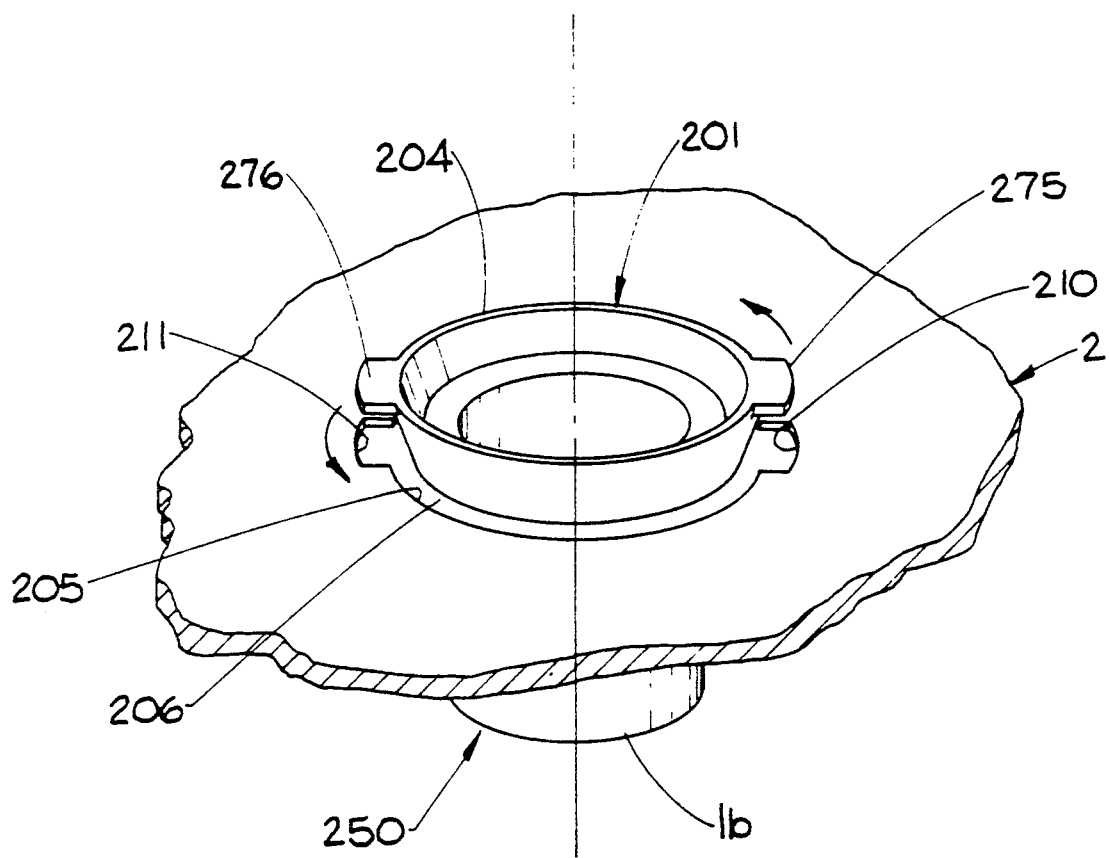
FIG. 10 is a simplified perspective view (shown in an inverted position for clarity) of still another spout embodiment of the present invention wherein a pair of opposing ears provided on the spout skirt are passed through a pair of coinciding keyways in the cut aperture so that the spout may thereafter be rotated to retain it within the aperture until the flange swaging and sealing operations have been performed.

In FIG. 10 there is shown still another fitment embodiment 250 of the present invention which is generally similar to fitment embodiment 50 shown in FIGS. 1–8. However the spout portion 201 of fitment embodiment 250 incorporates a pair of diametrically opposing ears 275,276 on the lowermost extremity of truncated skirt 204, which in all other respects is identical to truncated skirt 4 on spout 1.

The carton wall 2 shown in FIG. 10 includes a cut aperture 205 having a pair of opposing keyways 210,211 diametrically opposed from one another. The keyways 210,211 will permit passage of ears 275 and 276 on skirt 204 of spout 201 therethrough without interference. Once the skirt 204 of fitment 250 has been passed through the aperture 205 in carton wall 2, as generally shown in an inverted condition in FIG. 10, the fitment 250 may be rotated so as to misalign the ears 275 and 276 on skirt 204 with the keyways 210 and 211 in the carton wall aperture 205. So long as the ears 275 and 276 on skirt 204 remain misaligned with keyways 210 and 211, the fitment 250 will be retained by the aperture 205 in carton wall 2 until such time as skirt 204 is swaged to form an innermost flange having a portion coinciding with preformed outermost flange 206 and the two flanges are sealed to the opposing surfaces of the carton wall 2. So long as the maximum diameter of the swaged innermost flange formed from skirt 204 extends beyond the outermost portion of the keyways 210 and 211 of aperture 205, the cut edges of both aperture 205 and keyways 210 and 211 will be protected by the seals existing between the coinciding portions of the innermost and outermost flanges and the adjacent surfaces of the carton board.

As will be appreciated by those skilled in the art, the present invention may be practiced in conjunction with nearly any type of apertured container material wherein a layer of material which is capable of being sealed by the application of heat and pressure is provided on the opposing surfaces of the wall containing the aperture through which the spout must pass. Thus the material comprising the container may be a homogeneous thermoplastic material or it may be a layered laminate wherein the outermost surfaces of the material are thermoplastic in nature.

While the present invention has been described primarily in the context of a liquid container for products such as milk, juice or laundry additives, it is recognized that the present invention may also be practiced to advantage in many other applications and environments, e.g. cooking oils, salad dressings, motor oils, etc. It is further recognized that the configuration of that portion of the spout which is located on the exterior of the carton or package may be altered, as desired, without departing from the scope of the present invention. For example, the spout could be provided with securement means for attaching specialized dispensing apparatus such as funnels, measuring cups, spout extensions, etc. It will be obvious to those skilled in the art that various changes and modifications can be made without departing from the spirit and scope of the invention, and it is intended to cover in the appended claims all such modifications that are within the scope of this invention.

What is claimed is:

1. A method for securing a one-piece polymeric pouring spout having a liquid passageway including a discharge orifice and at least one preformed flange oriented substantially perpendicular to said liquid passageway along its length, said preformed flange having a truncated skirt exhibiting a minimum cross-section which is greater than the maximum cross-section of the exterior portion of the spout extending therefrom, in liquid tight relation to the innermost and outermost surfaces of a carton comprised of a laminate material having an intermediate layer comprised of paperboard and an innermost and outermost layer which are substantially impervious to liquid, said method comprising the steps of:

(a) cutting a hole of predetermined cross-section in a wall of said carton, thereby exposing said paperboard layer at the edges of said cut hole, said cross-section of said hole being large enough to fully insert said truncated skirt on said preformed flange of said one-piece polymeric pouring spout without damaging either said skirt or said carton wall, yet small enough to be totally blocked by said preformed flange on said pouring spout;

(b) inserting said truncated skirt on said preformed flange of said one-piece polymeric pouring spout through said cut hole in said wall of said carton so that said discharge orifice of said spout is on the exterior of said carton;

(c) bringing said preformed flange on said pouring spout into contacting relation with said carton wall about the periphery of said cut hole so as to block said cut hole in said carton wall;

(d) deforming said truncated skirt extending from said preformed flange of said pouring spout in an outward direction to form a second flange on the opposite surface of said carton wall about said cut hole, said second flange exhibiting a minimum cross-section which is substantially equal to or greater than the maximum cross-section of said pouring spout as measured at any point above said preformed flange and a maximum cross-section which is not only large enough to block said cut hole in said carton wall, but which is also large enough to coincide with at least a portion of said preformed flange located on the opposite surface of said carton wall; and (e) simultaneously applying sufficient heat and pressure to the coinciding portions of said opposing flanges and only the carton surfaces they contact to continuously fuse said coinciding portions of said flanges to the innermost and outermost layers of said carton wall about the periphery of said cut hole, whereby the exposed paperboard layer at the edges of said cut hole is completely isolated from the liquid contained in or dispensed from said carbon through said one-piece pouring spout as well as any liquid to which said carton is exposed from the environment through which it passes prior to emptying of its contents and disposal thereof.

2. The method of claim 1, wherein said heat and pressure are simultaneously applied to the coinciding portions of said opposing flanges by contacting said coinciding portions of said flanges with an ultrasonically vibrating horn on one side and a stationary anvil on the other.

3. A method for securing a one-piece polymeric pouring spout having a liquid passageway including a discharge orifice and at least one preformed flange oriented substantially perpendicular to said liquid passageway along its length, said preformed flange having a truncated skirt exhibits a minimum cross-section which is greater than the maximum cross-section of the exterior portion of the spout extending therefrom, in liquid tight relation to the innermost and outermost surfaces of a package having innermost and outermost layers which are substantially impervious to liquid, said method comprising the steps of:

(a) cutting a hole of predetermined cross-section in said package, thereby exposing the edges of said cut hole, said cross-section of said hole being large enough to fully insert said truncated skirt on said preformed flange of said one-piece polymeric pouring spout without damaging either said skirt or said carton wall, yet small enough to be totally blocked by said preformed flange on said pouring spout;

(b) inserting said depending truncated skirt on said preformed flange of said one-piece polymeric pouring spout through said cut hole in said package so that said discharge orifice of said spout is on the exterior of said package;

(c) bringing said preformed flange on said pouring spout into contacting relation with said package about the periphery of said cut hole so as to block said cut hole in said package;

(d) deforming said truncated skirt extending from said preformed flange of said pouring spout in an outward direction to form a second flange on the opposite surface of said package, said second flange exhibiting a minimum cross-section which is substantially equal to or greater than the maximum cross-section of said pouring spout as measured at any point above said preformed flange and a maximum cross-section which is not only large enough to block said cut hole in said package, but which is also large enough to coincide with at least a portion of said preformed flange located on the opposite surface of said package wall; and (e) simultaneously applying sufficient heat and pressure to only the coinciding portions of said opposing flanges and the package surfaces they contact to continuously fuse said coinciding portions of said flanges to the innermost and outermost layers of said package about the periphery of said cut hole, whereby the exposed edges of said cut hole are completely isolated from the liquid contained in or dispensed from said package through said one-piece pouring spout as well any liquid to which said package is exposed from the environment through which it passes prior to emptying of its contents and disposal thereof.

4. The method of claim 3, wherein said heat and pressure are simultaneously applied to the coinciding portions of said opposing flanges by contacting said coinciding portions of said flanges with an ultrasonically vibrating horn on one side and a stationary anvil on the other.

5. Apparatus for securing a one-piece polymeric pouring spout having a liquid passageway including a discharge orifice and at least one preformed flange oriented substantially perpendicular to said liquid passageway along its length, said preformed flange having a truncated skirt exhibiting a minimum cross-section which is greater than the maximum cross-section of the exterior portion of the spout extending therefrom, in liquid tight relation to the innermost and outermost surfaces of a carton comprised of a laminate material having an intermediate layer comprised of paperboard and an innermost and outermost layer which are substantially impervious to liquid, said apparatus comprising:

(a) means for cutting a hole of predetermined cross-section in a wall of said carton, thereby exposing said paperboard layer at the edges of said cut hole, said cross-section of said hole being large enough to fully insert said truncated skirt on said preformed flange of said one-piece polymeric pouring spout without damaging either said skirt or said carton wall, yet small enough to be totally blocked by said preformed flange on said pouring spout;

(b) means for inserting said depending truncated skirt on said preformed flange of said one-piece polymeric pouring spout through said cut hole in said wall of said carton so that said discharge orifice of said spout is on the exterior of said carton;

(c) means for bringing said preformed flange on said pouring spout into contacting relation with said carton wall about the periphery of said cut hole so as to block said cut hole in said carton wall;

(d) means for deforming said truncated skirt extending from said preformed flange of said pouring spout in an outward direction to form a second flange on the opposite surface of said carton wall about said cut hole, said deforming means exhibiting a cross-section which is at least equal to the maximum cross-section of said preformed flange, said second flange exhibiting a minimum cross-section which is substantially equal to or greater than the maximum cross-section of said pouring spout as measured at any point above said preformed flange and a maximum cross-section which is not only large enough to block said cut hole in said carton wall, but which is also large enough to coincide with at least a portion of said preformed flange located on the opposite surface of said carton wall; and (e) means for simultaneously applying sufficient heat and pressure to only the coinciding portions of said opposing flanges and the carton surfaces they contact to continuously fuse said coinciding portions of said flanges to the innermost and outermost layers of said carton wall about the periphery of said cut hole, whereby the exposed paperboard layer at the edges of said cut hole is completely isolated from the liquid contained in or dispensed from said carton through said one-piece pouring spout as well any liquid to which said carton is exposed from the environment through which it passes prior to emptying of its contents and disposal thereof.

6. The apparatus of claim 5, wherein said means for simultaneously applying heat and pressure to the coinciding portions of said opposing flanges comprises an ultrasonically vibrating horn and a supporting anvil.

7. Apparatus for securing a one-piece polymeric pouring spout having a liquid passageway including a discharge orifice and at least one preformed flange oriented substantially perpendicular to said liquid passageway along its length, said preformed flange having a truncated skirt exhibiting a minimum cross-section which is greater than the maximum cross-section of the exterior portion of the spout extending therefrom, in liquid tight relation to the innermost and outermost surfaces of a package having innermost and outermost layers which are substantially impervious to liquid, said apparatus comprising:

(a) means for cutting a hole in said package, thereby exposing the edges of said cut hole, said hole being large enough to fully insert said liquid passageway of said one-piece polymeric pouring spout without damaging either said skirt or said carton wall, wet small enough to be totally blocked by said preformed flange on said pouring spout;

(b) means for inserting said liquid passageway of said one-piece polymeric pouring spout through said cut hole in said package so that said discharge orifice of said spout is on the exterior of said package;

(c) means for bringing said preformed flange on said pouring spout into contact relation with said package about the periphery of said cut hole so as to block said cut hole in said carton wall;

(d) means for deforming said liquid passageway of said pouring spout to form a second flange on the interior of said package, said deforming means exhibiting a cross-section which is at least equal to the maximum cross-section of said preformed flange, said second flange exhibiting a minimum cross-section which is substantially equal to or greater than the maximum cross-section of said pouring spout as measured at any point above said preformed flange and a maximum cross-section which is not only large enough to block said cut hole in said package, but which is also large enough to coincide with at least a portion of said preformed flange on the opposite surface of said package; and (e) means for simultaneously applying sufficient heat and pressure to only the coinciding portions of said opposing flanges and the package surfaces they contact to continuously fuse said coinciding portions of said flanges to the innermost and outermost layers of said package about the periphery of said cut hole, whereby the exposed edges of said cut hole are completely isolated from the liquid contained in or dispensed from said package through said one-piece pouring spout as well any liquid to which said package is exposed from the environment through which it passes prior to emptying of its contents and disposal thereof.

8. The apparatus of claim 7, wherein said means for simultaneously applying heat and pressure to the coinciding portions of said opposing flanges comprises an ultrasonically vibrating horn and a supporting anvil.

* * * * *

UNITED STATES PATENT AND TRADEMARK OFFICE
CERTIFICATE OF CORRECTION

PATENT NO. : 5,125,886

DATED : December 15, 1989

INVENTOR(S) : WILLIAM P. DIRKSING

It is certified that error appears in the above-identified patent and that said Letters Patent is hereby corrected as shown below:

On the title page:

In the ABSTRACT, line 1, delete "carbon" and insert therefor -- carton -- .

In the "References Cited" section after
"4,909,434  3/1990  Jones et al. ......... 493/133" please insert --

| | | | |
|---|---|---|---|
| 1,095,535 | 5/1914 | Weis | |
| 1,357,304 | 11/1920 | Valdes | 229/125.15 |
| 1,165,229 | 12/1915 | Davis | |
| 2,104,744 | 11/1938 | Hothersall | 221/23 |
| 2,142,293 | 1/1939 | Waite | 221/60 |
| 2,156,366 | 5/1939 | Volk | 229/17 |
| 2,185,284 | 1/1940 | Wilson | 221/62 |
| 2,198,564 | 4/1940 | Robison | 221/78 |
| 2,201,332 | 5/1940 | Bensel | 229/43 |
| 2,400,716 | 5/1946 | Sattler | 229/125.15 |
| 2,418,659 | 4/1947 | Nyden | 222/498 |
| 2,543,909 | 3/1951 | Hatheway, Jr. | 222/566 |
| 2,670,885 | 3/1954 | Allen | 222/569 |
| 2,687,831 | 8/1954 | Miller | 222/569 |
| 2,690,861 | 10/1954 | Tupper | 222/498 |
| 2,820,581 | 1/1958 | Makuta | 222/528 |
| 2,946,478 | 7/1960 | Clair, Jr. et al | 220/54 |
| 2,972,184 | 2/1961 | Andrew | 29/208 |
| 3,016,168 | 1/1962 | Larson | 222/189 |
| 3,029,009 | 4/1962 | Hill | 229/17 |
| 3,239,112 | 3/1966 | Porcelli | 220/258 |
| 3,282,477 | 11/1966 | Henchert | 222/541 |
| 3,300,106 | 1/1967 | Chmela | 222/517 |
| 3,334,797 | 8/1967 | Latham et al | 229/7 |

UNITED STATES PATENT OFFICE
CERTIFICATE OF CORRECTION

PATENT NO. : 5,125,886    Page 2 of 5
DATED : December 15, 1989
INVENTOR(S) : WILLIAM P. DIRKSING It is certified that error appears in the above-identified patent and that said Letters Patent is hereby corrected as shown below:

| | | | |
|---|---|---|---|
| 3,412,919 | 11/1968 | Cain | 229/7 |
| 3,458,080 | 7/1969 | Laurizio | 220/27 |
| 3,481,515 | 12/1969 | Booth et al | 222/529 |
| 3,608,771 | 9/1971 | Monroe et al | 220/27 |
| 3,642,047 | 2/1972 | Waage | 150/8 |
| 3,659,756 | 5/1972 | Lancaster | 222/531 |
| 3,756,448 | 9/1973 | Moller et al | 220/53 |
| 3,923,203 | 12/1975 | Anderson, Jr | 222/153 |
| 3,924,777 | 12/1975 | Peyser | 220/277 |
| 3,933,297 | 1/1976 | Carlsson et al | 229/3.1 |
| 3,968,872 | 7/1976 | Cavazza | 206/222 |
| 3,977,591 | 8/1976 | Martensson et al | 229/7R |
| 3,990,603 | 11/1976 | Brochman | 220/260 |
| 3,998,354 | 12/1976 | Song | 220/269 |
| 4,122,970 | 10/1978 | Amabili | 220/256 |
| 4,141,477 | 2/1979 | Hengesbach | 222/569 |
| 4,174,051 | 11/1979 | Edwards et al | 222/105 |
| 4,214,675 | 7/1980 | Schmit | 222/83 |
| 4,227,629 | 10/1980 | Froyman | 222/566 |
| 4,231,488 | 11/1980 | Ward et al | 220/288 |
| 4,241,855 | 12/1980 | Yoshioka | 222/479 |
| 4,244,491 | 1/1981 | Takahashi et al | 229/125.14 |
| 4,266,993 | 5/1981 | Olsen | 156/69 |
| 4,344,472 | 8/1982 | Larkin et al | 150/8 |
| 4,363,420 | 12/1982 | Andrews | 220/307 |
| 4,397,401 | 8/1983 | Ueno et al | 220/260 |
| 4,448,326 | 5/1984 | Brochman | 220/270 |
| 4,483,464 | 11/1984 | Nomura | 222/83 |
| 4,488,661 | 12/1984 | Homma | 220/462 |
| 4,498,588 | 2/1985 | Scott | 206/526 |

UNITED STATES PATENT AND TRADEMARK OFFICE
CERTIFICATE OF CORRECTION

PATENT NO. : 5,125,886

DATED : December 15, 1989

INVENTOR(S) : WILLIAM P. DIRKSING

It is certified that error appears in the above-identified patent and that said Letters Patent is hereby corrected as shown below:

```
D277,826     3/1985    Brown, Sr...........D9/439
4,520,940    6/1985    Boyd et al..........220/68
4,526,287    7/1985    Miyamatsu et al.....220/260
4,533,071    8/1985    Uhlig...............222/498
4,553,693    11/1985   Terajima et al......229/7S
4,555,037    11/1985   Rhees...............220/258
4,570,826    2/1986    Fattori.............222/83
4,582,216    4/1986    Byrd................220/260
4,588,105    5/1986    Schmitz et al.......220/359
4,595,116    6/1986    Carlsson............220/359
4,604,850    8/1986    Reil................53/423
4,605,136    8/1986    Debetencourt........215/232
4,624,392    11/1986   Malpas et al........222/83
4,669,640    6/1987    Ando et al..........222/541
4,705,197    11/1987   Gordon et al........206/604
4,723,689    2/1988    Vallos et al........222/91
4,730,769    3/1988    Stark...............229/125.15
4,733,786    3/1988    Emslander...........215/232
4,753,832    6/1988    Brown et al.........229/176
4,813,578    3/1989    Gordon et al........220/258
4,830,273    5/1989    Kalberer et al......229/123.1
4,834,728    5/1989    McKenna.............604/301
4,887,765    12/1989   Rausing.............229/123.2
4,909,434    3/1990    Jones et al.........229/125.15
4,964,562    10/1990   Gordon..............229/125.15
```

UNITED STATES PATENT AND TRADEMARK OFFICE
CERTIFICATE OF CORRECTION

PATENT NO. : 5,125,886

DATED : December 15, 1989

INVENTOR(S) : WILLIAM P. DIRKSING

It is certified that error appears in the above-identified patent and that said Letters Patent is hereby corrected as shown below:

Foreign Patents

| | | |
|---|---|---|
| 534911 | 12/1956 | Canada |
| 1191109 | 10/1959 | France |
| 1093722 | 11/1960 | E. Germany |
| 1349783 | 4/1964 | France |
| 964860 | 7/1964 | London |
| 984756 | 3/1965 | United Kingdon |
| 1395697 | 3/1965 | France |
| 2659275 | 7/1978 | Germany |
| 0018325 | 10/1980 | Europe |

These references have been considered by the Examiner as reflected by the Examiner's initials and signature on the form PTO-1449 dated June 10, 1992.

Column 7, line 2, after "particularly" delete -- i --

Column 8, line 26, delete "refracted" and insert therefor -- retracted --

Column 9, line 8, delete "layer" and insert therefor -- layers -- .

UNITED STATES PATENT AND TRADEMARK OFFICE
CERTIFICATE OF CORRECTION

PATENT NO. : 5,125,886
DATED : December 15, 1989
INVENTOR(S) : WILLIAM P. DIRKSING It is certified that error appears in the above-identified patent and that said Letters Patent is hereby corrected as shown below:

Column 9, line 16, after "in" insert -- the -- .

Column 10, line 2, after "spout" insert -- 1 -- .

Column 14, lines 30-31, delete "carbon" and insert therefor -- carton -- .

Column 16, line 26, after "well" insert -- as -- .

Column 16, line 50, delete "wet" and insert therefor -- yet -- .

Column 16, line 59, delete "contact" and insert therefor -- contacting -- .

Signed and Sealed this

Twenty-first Day of September, 1993

Attest:

BRUCE LEHMAN

*Attesting Officer*     *Commissioner of Patents and Trademarks*